United States Patent [19]

Benkovic et al.

[11] Patent Number: 4,900,674
[45] Date of Patent: Feb. 13, 1990

[54] ANTIBODY COMBINING SITES THAT EXHIBIT AMIDE OR ESTER SYNTHASE ACTIVITY

[75] Inventors: Stephen Benkovic, State College, Pa.; Richard A. Lerner, La Jolla; Alfonso Tramontano, San Diego, both of Calif.; Andrew D. Napper, State College, Pa.

[73] Assignee: Scripps Clinic and Research Foundation, La Jolla, Calif.

[21] Appl. No.: 55,177

[22] Filed: May 28, 1987

[51] Int. Cl.[4] .................... C12N 9/88; C12N 9/00; C12P 17/06; C07K 15/00

[52] U.S. Cl. .................................... 435/232; 435/183; 435/125; 530/387; 530/388

[58] Field of Search ............... 435/183, 196, 232, 125; 530/387, 388, 389

[56] References Cited

U.S. PATENT DOCUMENTS 4,659,567  4/1987  Tramontano et al. ................ 424/85
4,792,446  12/1988  Kim et al. ........................... 424/183

FOREIGN PATENT DOCUMENTS 8502414  6/1985  PCT Int'l Appl. .

OTHER PUBLICATIONS

Tramontano, A., et al., (1986), Science 234, 1566–1570.
Bartlett, P. A., et al., (1983), Biochem. 22, 4618–4624.
Raso, V., et al., (1973), J. Am. Chem. Soc. 95(5), 1621–1628.
Proceedings of the XVIIIth Solvay Conference on Chemistry, Brussels, Nov. 28–Dec. 1, 1983, "Antibodies of Predetermined Specificity in Biology and Medicine" Richard Alan Lerner, pp. 43–49.
Jencks, W. P., "Catalysis In Chemistry And Enzymology", McGraw-Hill Book Company (1969), pp. 287–289.
Slobin, Biochem., 5:2836–2844 (1966).
Kohen et al., FEBS Letters, 100:137–140 (1979).
Kohen et al., Biochim. Biophys. Acta, 629:328–337 (1980).
Kohen et al., FEBS Letters, 111:427–430 (1980).
Royer, Adv. Catal., 29:197–227 (1980).
Jenks, Adv. Enzymol., 43:313–317 (1975).
Lerner, Adv. Imm. 36:1–44 (1984).
Tramontano et al., Proc. Natl. Acad. Sci. U.S.A., 83:6736–6740 (1986).
Pollack et al., Science, 234: 1570–1573 (1986).
Marx, Science, 234: 1497–1498 (1986).
Anon., Chemical & Engineering News, Dec. 15, 1986, p. 6.
Hansen, Nature, 325:304 (1987).
Anon., Scientific American, 256(2):84–85 (Feb. 1987).
Baum, Chemical & Engineering News, Apr. 6, 1987, pp. 30–33.
Napper et al., Science, 237: 1041–1043 (1987).
Lerner et al., TIBS, 12:427–430 (1987).
Stinson, Chemical & Engineering News, Oct. 19, 1987, pp. 30–33.
Janda et al., Science, 241:1188–1191 (1988).
Marx, Science, 241:1164 (1988)
Anon, Chemistry & Engineering News, Sep. 5, 1988, p. 14.
Vogel, Discover, 9:38–43 (Oct. 1988).
Massey, Nature, 328:457–458 (Jul. 1987).
Benkovic et al., Proc. Natl. Acad. Sci. U.S.A., 85:5355–5358 (Aug. 1988).
White et al., Principles of Biochemistry, McGraw-Hill Book Company, New York (1978), p. 202.
Hogness et al., Qualitative Analysis And Chemical Equilibrium, 4th ed., Holt, Reinhart and Winston, Inc., New York (1954), p. 565.
Raso et al., Biochem.1, 14:591–599.
Raso et al., Biochem., 14:584–591.

Primary Examiner—Jayme A. Huleatt
Assistant Examiner—Charles L. Patterson, Jr.
Attorney, Agent, or Firm—Dressler, Goldsmith, Shore, Sutker & Milnamow, Ltd.

[57] ABSTRACT

A phosphorous-containing analog-ligand having a conformation that substantially corresponds to the conformation of an amide- or ester-forming transition state is used to induce production of receptor molecules whose antibody combining sites have amide or ester synthase catalytic activity when reacted with a ligand containing (i) a carbonyl carbon atom and (ii) an amine or alcohol group that are structurally capable of forming a preselected carboxylic amide or ester bond.

6 Claims, 2 Drawing Sheets

ANTIBODY COMBINING SITES THAT EXHIBIT AMIDE OR ESTER SYNTHASE ACTIVITY

TECHNICAL FIELD

The present invention relates to antibodies, antigens and immunogens, and more particularly to antibody molecules that contain a combining site that binds and thereby stabilizes the tetrahedral carbon atom of an amide- or ester-forming transition state and exhibits catalytic properties.

BACKGROUND OF THE INVENTION

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding can lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively. In addition, such binding can lead to formation of amide and ester bonds in the formation of proteins and fats.

Immunological binding may be used to experimentally divert binding interactions to catalytic processes. Jencks, W. P., *Catalysis in Chemistry and Enzymology*, page 288 (McGraw-Hill, New York 1969). Attempts to introduce reactive groups into a combining site of an antibody, however, have been unsuccessful. Royer, G. P., *Adv. Catal.*, 29, 197 (1980). Some monoclonal antibodies are reported to include nucleophilic residues which react with an activated ester appendage on a homologous hapten recognized by the antibody. Kohen et al., *FEBS Lett.*, 111, 427 (1980); Kohen et al., *Biochem. Biophys. Acta*, 629, 328 (1980) and Kohen et al., *FEBS Lett.*, 100, 137 (1979). In these cases, the rate of acylation of the nucleophile is presumably accelerated by its proximity to a binding site of the haptenic fragment.

These constructs, though interesting, are severely limited by the failure to address the mechanism of binding energy utilization which is essential to enzymes [W. P. Jencks, *Adv. Enzymol.*, 43, 219 (1975)]. Aside from this, when strong binding is directed to stable states, the slow rate of dissociation of the complex will impede catalysis. These deficiencies can be redressed by using a transition state analog as the hapten to elicit the desired antibodies. This hapten (also referred to herein as an "analog-ligand") would assume the role of an inhibitor in the catalytic system.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable.

Although the above hydrolytic transition states can not be isolated, a large amount of scientific literature has been devoted to the subject. Some of that literature is discussed hereinafter.

While the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood. It would therefore be beneficial if the topology of a plurality of binding sites were known so that the interactions of the ligands that bind in those sites could be studied. Unfortunately, the topology of receptor binding sites in biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity; i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

More recently, Lerner, Tramontano and Janda [*Science*, 234, 1566 (1986)] reported monoclonal antibodies that catalytically hydrolyzed an ester. Tramontano and Lerner, also describe using monoclonal antibodies to hydrolyze esters in U.S. Pat. No. 4,656,567. Schultz, Pollack and Jacobs [*Science*, 234, 1570 (1986)] reported monoclonal antibodies that catalyze the hydrolysis of a carbonate.

In the two Lerner and Tramontano disclosures, the antibodies were raised to a phosphonate that was synthesized to represent a stable analog of the tetrahedral hydrolytic transition state of the carboxylic acid ester or carbonate ester. The Schultz et al. antibody was a myeloma protein that happened to bind to a phosphonate that was structurally analogous to the carbonate analog hydrolyzed.

BRIEF SUMMARY OF THE INVENTION

The present invention contemplates a catalytic molecule. That molecule contains an antibody combining site that itself contains the catalytically active portion of the molecule. An antibody combining site can also be referred to as a paratope or an idiotype-containing polyamide. The catalytic molecule is generally referred to herein as a receptor molecule, or more simply, a receptor.

A receptor molecule of the present invention is preferably monoclonal (discussed hereinafter), and contains an antibody combining site that is capable of catalyzing the formation of a preselected carboxylic amide or ester bond, preferably a lactone bond.

In enzymology, a protein that catalyzes such an amide- or ester-forming reaction can be said to be a member of the amide or ester synthase family of enzymes. Using that nomenclature system for the preferred formation of a lactone, a lactone-forming enzyme can be referred to as a lactone synthase. The monoclonal receptors of this invention will be described herein as exhibiting amide or ester synthase activity when discussed broadly, and will be described as exhibiting lactone synthase activity when discussed in realtion to the specific reactions described herein as exemplary.

Thus, the present invention contemplates a molecule exhibiting amide or ester synthase activity that comprises a receptor molecule. The preferably monoclonal receptor contains an antibody combining site capable of catalyzing the formation of a preselected carboxylic amide or ester bond. The combining site binds: (a) to a ligand containing a carbonyl carbon atom and an amine or alcohol group that are structurally capable of forming the preselected carboxylic amide or ester bond; and (b) to a ligand structurally analogous to the preselected amide or ester; the analog-ligand having a tetrahedrally bonded phosphorous atom located at the position occupied by the above-mentioned carbonyl carbon atom of the preselected carboxylic amide or ester bond of the before-mentioned ligand. The tetrahedrally bonded phosphorous atom is itself directly bonded to: (i) the alpha-carbon atom of the acid portion of the ligand by a single bond; (ii) a first oxygen atom that is doubly bonded to the phosphorus atom; (iii) a second oxygen atom that is bonded to the phosphorous atom by a single bond, and is singly bonded to a radical selected from the group consisting of $C_1$–$C_6$ lower alkyl, benzyl and phenyl; and (iv) a third oxygen atom or a nitrogen atom singly bonded to the phosphorous atom, and is also singly bonded to the alpha-carbon atom of the amine or alcohol portion of the ligand.

In preferred practice, the molecule exhibits lactone synthase activity. Thus, the ligand containing the carbonyl carbon is capable of forming a lactone, and the analog ligand is a phosphonate lactone. In particularly preferred practice, the ligand and analog-ligands have structures of formulas I and II, respectively, below:

wherein R is hydrogen, $C_1$–$C_6$ lower alkyl or a linking group bonded to an antigenic carrier; and $R^2$ is hydrogen or $C_1$–$C_6$ lower alkyl.

A method of forming a preselected carboxylic acid amide or ester constitutes still another aspect of the present invention. Here, a ligand containing a carbonyl atom and an amine or alcohol group capable of forming the preselected carboxylic acid amide or ester is admixed in an aqueous medium with an effective amount of a before-described amide or ester synthase molecule to form a reaction mixture. The reaction mixture is thereafter maintained for a time period sufficient for the ester or amide to form; and the product is thereafter preferably recovered.

It is thus to be appreciated that the invention, in a broader sense, contemplates a ligand capable of forming an amide or ester as well as an analog-ligand containing an analog to the amide- or ester-forming transition state of the amide or ester product. Those molecules differ in the fact the ligand contains a carbonyl group and an amine or alcohol capable of forming an amide or ester, whereas the ligand-analog contains a phosphorous central atom in a structure that mimics the amide- or ester-forming transition state. The ligand and analog-ligand can also differ in the substitution of the atoms bonded to the central atom at at least one position away from the central atom since the analog-ligand must possess sufficient stability to be used as an immunizing hapten, and be bound to an antigenic carrier.

In the studies described herein, phosphonate monoaryl esters function as transition state analogs to generate monoclonal antibodies that exhibit amide or ester synthase activity, and specifically, lactone synthase activity. In effect, these antibodies express their inherent binding energy functionally, as true enzymes, to form an amide or ester (lactone) and classically, as antibodies, to bind antigens.

A exemplary immunizing analog-ligand molecule that contains an analog of a lactone-forming transition state is represented by the formula:

wherein

X is O or NH;

R is hydrogen, $C_1$-$C_6$ lower alkyl, or a linking group alone or bonded to an antigenic carrier; and $R^1$ is $C_1$-$C_6$ lower alkyl, benzyl or phenyl.

The analog-ligand hydrolytic transition state molecules are also contemplated in this invention. These molecules are of relatively small molecular size and are therefore typically linked to a larger, antigenic carrier molecule when used to induce the production of a receptor molecule. Such relatively small molecules are commonly referred to as haptens. These analog-ligand molecules also typically contain a linking atom or group such as a reactive mercaptan or a succinimide group that provides a means to attach the haptenic analog-ligand molecules to an antigenic carrier for use as an immunogen, as shown in the formula above.

A method of preparing a particular amide or ester synthase is also contemplated. Here, a before-described haptenic analog-ligand molecule containing an amide- or ester-forming transition state analog is provided linked to an antigenic carrier as an immunogenic conjugate. The conjugate thus provided is dissolved or dispersed in a physiologically tolerable diluent to form an inoculum. The inoculum is introduced as by injection into a mammalian host in an amount sufficient to induce antibodies to the haptenic analog-ligand. The antibodies so induced are harvested. The harvested antibodies that immunoreact with the immunizing, haptenic analog-ligand are then collected.

In particularly preferred practice, monoclonal antibodies are prepared. Here, the above immunizing technique is used and the harvested antibodies are assayed for their ability to bind to (immunoreact with) the immunizing, haptenic ligand analog. Immunoglobulin-producing cells such as those from the spleen of an animal whose antibodies bind to the immunizing, haptenic analog-ligand are collected and are fused with myeloma cells to form hybridoma cells. The hybridoma cells are grown in a culture medium and the supernatant medium from the growing hybridoma cells is assayed for the presence of antibodies that bind to the immunizing, haptenic analog-ligand. Hybridoma cells whose supernatant contains such binding antibodies are then cloned to provide the desired monoclonal antibodies from culture medium supernatant or from the ascites of a host mammal into which the hybridoma is introduced.

The described polyclonal or monoclonal antibodies can be used as the synthase molecules of this invention. Alternatively, the so-called Fc or Fc' portions of the antibodies can be removed as by enzymic cleavage to provide an antibody combining site (paratope or idiotype-containing polyamide) that binds to the immunizing, haptenic analog-ligand such as Fab or F(ab')$_2$ antibody portion, respectively.

The polyclonal, monoclonal and idiotype-containing polyamide receptors also bind to the ligand capable of forming the amide or ester. Such binding typically leads to catalyzed formation of the preselected amide or ester bond.

The present invention provides several benefits and advantages. One benefit is the preparation of receptors whose binding site topological requirements are tailored to a particular ligand to be studied.

Another benefit of the present invention is the preparation of receptors that form the amide or ester bondat a predetermined site and that exhibit catalytic properties.

An advantage of the invention is that because of the specificity of the receptors that can be produced, a ligand containing a plurality of different reactive groups capable of forming amide or ester bonds can be caused to form the desired bond at a preselected, particular site.

Still further benefits and advantages of the present invention will be apparent to those skilled in the art from the disclosures that follow.

BRIEF DESCRIPTION OF THE DRAWINGS

In the drawings, which constitute a portion of this disclosure:

FIG. 1 is a schematic representation showing a ligand capable of forming a lactone (on the left), a proposed lactone-forming transition state for the ligand (bracketed, upper center), a structure of the analog-ligand (bracketed, lower center), and the lactone product of the reaction of the ligand (on the right). The sterochemistry of one ligand enantiomer, the transition state and analog-ligand, and product are illustrated to show one possible stereochemical pathway. In that stereochemical view, solid lines are in the plane of the page, bonds projecting outwardly from the plane are shown by solid triangular bonds, bonds projecting backwardly from the page are shown by a dashes, and a bond being formed is shown as a dotted line. The symbols $\delta^-$ and $\delta^+$ are utilized to show relative negative and positive charges, and the symbol $\neq$ designates the transition state.

DETAILED DESCRIPTION OF THE INVENTION

I. Introduction

The present invention relates to the production of antibodies and idiotype-containing polyamide (antibody combining site) portions induced by analogs that mimic the conformation of chemical intermediates in the reaction sequence for the formation of an ester or an amide bond, and particularly to the formation of a lactone bond. The antibodies and idiotype-containing polyamides bind to the amide- or ester-forming transition state of a preselected portion of a ligand and exhibit catalytic properties.

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, whereas a non-catalytic complex is the usual result of antibody-antigen binding.

Enzymes are believed to catalyze the reactions of proteins by combining with the protein to stabilize the transition state of the reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W. P., *Adv. Enzymology*, 43, 219 (1975) and Pauling, L., *Amer. Scientist*, 36, 58 (1948)]. Support for this theory comes from the observation that substances that are thought to model the presumed transition states are often strongly bound to the enzymes as competitive inhibitors. Leinhard, G., *Science*, 180, 149 (1973) and Wolfenden, R., *Acc. Chem. Res.*, 5, 10 (1972). It is further thought that the enzyme accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W. P., *XVII International Solvay Conference* (November 1983)].

The converse proposition is that a receptor that is prepared to optimally bind a suitable analog of a transition state would function as a catalyst. The demonstration of this result as shown herein completes the correlation of enzyme function and receptor structure, and provides a useful; approach to devising artificial enzymes.

The basic idea behind immunological bond formation described herein contemplates the use of analog-ligands in the preparation of antibodies of predetermined specificity that preferentially bind to and thereby stabilize the transition state of amide or ester bond formation upon binding to the specified ligand. The analog-ligands simulate the conformation of high energy transition state intermediates in amide or ester formation to induce the production of antibodies having the ability to bind to and catalyze bond formation in the ligand substrate.

Such preferential binding and stabilization results in a reduction in the activation energy for the bond-forming reaction, thus meeting a criterion for catalysis. Antibodies that display this property can be obtained by immunization with synthetic analogs that are chemically modified to resemble the bonding characteristics of a substrate ligand undergoing bond formation; i.e., by immunization with transition state analogs of the particular bond-forming reaction.

The mechanism by which an antibody forms an ester or amide bond of a bound ligand can be thought of in terms of an "induced fit" model. As the loosely bound substrate distorts or rearranges to conform to the binding geometry of the antibody combining site, stress can be relieved by chemical reorganization of a carbonyl carbon and an amine or alcohol of the ligand such that this reorganization leads to the formation of the desired bond.

The term "receptor" is used herein to mean a biologically active molecule that binds to a ligand and to an analog-ligand. The receptor molecules of the present invention are antibodies, substantially intact antibodies or idiotype-containing polyamide (paratopic) portions of an antibody. Biological activity of a receptor molecule is evidenced by the binding of the receptor to its antigenic ligand or analog-ligand upon their admixture in an aqueous medium, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polyamide portions (paratopes or antibody combining sites) of antibodies are those portions of antibody molecules that include the idiotype, and bind to the ligand or analog-ligand. Such portions include the Fab, Fab' and F(ab')$_2$ fragments prepared from antibodies by well-known enzymatic cleavage techniques. See for example, U.S. Pat. No. 4,342,566 to Theofilopoulos and Dixon. Inasmuch as the antibodies from which idiotype-containing polyamides are obtained are described as raised against or induced by immunogens, idiotype-containing polyamide receptors are also discussed as being "raised" or "induced" with the understanding that a cleavage step is required to obtain an idiotype-containing polyamide from an antibody. Intact antibodies are preferred, however, and will be utilized as illustrative of the receptor molecules of this invention.

The receptors useful in the present invention are more preferably monoclonal antibodies. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monclonal antibodies of the present invention are well known. Such receptors were first described by Kohler and Milstein, *Nature*, 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

As described herein, chemical analogs of ester ligands have been synthesized that incorporate phosphonate moieties at specific, predetermined sites to mimic the conformation of the transition state in the formation of an amide or ester bond. Such analogs are suitable candidates for this investigation because it is known that phosphonamidates have been used as transition state analogs in the inhibition of proteolytic enzymes [Bartlett, et. al., *Biochemistry*, 22, 4618 (1983)].

Short polypeptide chains can induce the production of antibodies that recognize and bind to a homologous protein at a predetermined specific site. The present invention carries the earlier work with polypeptides a major step forward. Here, the antibodies (receptors) are induced by an immunizing haptenic first molecule (the analog-ligand), and recognize and bind not only to that first molecule, but also to a second, related molecule (the ligand). In binding that second molecule, the receptor causes bond formation (which as demonstrated herein can be catalytic) of a preselected, ester or amide bond that corresponds in topology to the topology of the immunizing, haptenic first molecule. The correspondence in topology; i.e., size, shape and charge, provides a means for preselecting, the site at which hydrolysis of the ligand occurs.

Consequently, by synthesis of a relatively small, immunizing haptenic analog-ligand, one can induce the production of receptor molecules that recognize, bind to and catalytically form an ester or amide bond in a larger molecule that can contain a plurality of amide or ester bonds. Thus, a receptor can be prepared that causes formation of a selected, predetermined amide or ester bond. The implication of this result is that one can confer the activity of hitherto unknown synthases to immunoglobulins.

Furthermore, the activity of the antibody can be directed to any predetermined site at will by designating the amide or ester bond to be formed with the phosphonamidate or phosphonate configuration in the haptenic analog-ligand used for immunization.

II. Transition State of Bond Formation and Hapten (Analog-Ligand) Design

Amide or ester bond formation reactions catalyzed by a synthase of the present invention are in some ways analogous to transacylation processes that are characterized by carbonyl addition-elimination mechanisms. The acyl group may, therefore, possess varying degrees of tetrahedral character in this transition state. W. P. Jencks, *Catalysis in Chemistry and Enzymology*, ch. 10, (McGraw-Hill, New York, 1969). The enzymes that catalyze transacylation reactions might be expected to bind well those analogs of the ligand having a tetrahedral configuration about the acyl center. This is true for serine proteases, where a covalent bond between the ligand and the enzyme is formed temporarily [Westerik et al., *J. Biol. Chem.*, 247, 8195 (1972); R. C. Thompson, *Biochemistry*, 12, 47 (1973) and Imperial et al., *Biochemistry*, 25, 3760 (1986)], as well as for enzymes which catalyze the direct hydration of amides or esters. The latter category is inhibited by compounds with a tetrahedral configuration including a phosphate, phosphonate or phosphonamidate group in lieu of the scissile amide unit [Weaver et al., *J. Mol. Biol.*, 114, 119 (1977) and Jacobsen et al., *J. Am. Chem. Soc.*, 103, 654 (1981)].

Naturally occurring and synthetic substances containing phosphorus have been studied as inhibitors of metallopeptidases. In these enzymes, the transition state would appear to contain the hydrated amide in the coordination sphere of the metal ion [W. N. Lipscomb, *Acc. Chem. Res.*, 15, 232 (1982)]. A complete picture of a transition state analog might then have the phosphono group of an inhibitor as a ligand to a metal ion or some other polarizing site (see FIG. 1) [Weaver et al., *J. Mol. Biol.*, 114, 119 (1977) and Christianson et al., *J. Am. Chem. Soc.*, 108, 545 (1986)]. The role of the metal ions in metallopeptidases, however, is not clearly understood. It may have a multiple function in amide hydrolysis where proton transfer steps among the tetrahedral intermediates may be rate-limiting [L. M. Sayre, *J. Am. Chem. Soc.*, 108, 1632 (1986)].

The formation of a carboxylic amide or ester is a simple example of acylation that should also be approximated by the phosphonate-containing analog of the transition state. The binding of the charged phosphonate group may describe a stabilizing interaction in the transition state which would lead to catalysis. Amide and ester formation reactions generally do not proceed at convenient spontaneous rates under ambient conditions that are suitable for antibodies. Therefore, any bond formation (or loss of substrate) can be readily detected.

The structures of the analog-ligands and ligands for this investigation were selected according to certain criteria. These included the availability and stability of the organophosphorus precursors, the corresponding carboxylic acid substrate, the convenience of the chemical synthesis for its preparation, and the adaptability to diverse schemes for immunological presentation.

An exemplary basic molecular unit for the analog-ligand that provides the structural features necessary for inducing production of a lactone synthase is the phosphorus-containing lactone of formula III that is shown below:

III wherein
X is O or NH;
R is selected from the group consisting of hydrogen, $C_1$–$C_6$ lower alkyl and a linking group alone or bonded to an antigenic carrier; and
$R^1$ is selected from the group consisting of $C_1$–$C_6$ lower alkyl, benzyl and phenyl.

As is apparent from the above formula, when X is an oxygen atom (O), the analog-ligand is a lactone (phosphonate lactone), whereas when, X is a nitrogen atom bonded to a hydrogen atom (NH) the analog-ligand is a lactam (phosphonamidate lactone).

An analog-ligand of the above formula can be linked to an antigenic carrier molecule through an appropriate linking group R. Specific linking groups and antigenic carrier molecules are discussed hereinafter.

A particularly preferred analog-ligand hss a structure represented by formula II, below:

II wherein R is selected from the group consisting of hydrogen, $C_1$–$C_6$ lower alkyl, and a linking group alone or bonded to an antigenic carrier molecule.

When used as an immunogen, the R group of the haptenic analog-ligand is preferably a linking group bonded to an antigenic carrier, as described hereinafter. When used as an inhibitor, as in the studies shown in FIG. 2, the R group is perferably methyl ($C_1$ alkyl).

The ligand (substrate) structurally capable of forming an amide or ester bond and that contains a carbonyl carbon atom and an amine or alcohol group can be a single molecule that contains both of the reactive functionalities, or those functionalities (carbonyl carbon and amine or alcohol) can be on separate molecules. The singular form of the word "ligand" is utilized for both the single and two molecule species since once bound either type of those entities behaves as a single molecule.

A preferred ligand capable of forming a lactam or a lactone corresponding to the analog-ligand of formula III has a structure of formula IV, below:

wherein X and $R^1$ are as before-described, and $R^2$ is hydrogen for $C_1$–$C_6$ lower alkyl, preferably methyl ($C_1$)

A particularly preferred ligand of formula IV is the ligand that has the structure of formula I, below:

wherein $R^2$ is as described before.

Thus, the present invention contemplates a molecule exhibiting amide or ester synthase activity that comprises a receptor molecule. The preferably monoclonal receptor contains an antibody combining site capable of catalyzing the formation of a preselected carboxylic amide or ester bond. The combining site binds: (a) to a ligand containing a carbonyl carbon atom and an amine or alcohol group that are structurally capable of forming the preselected carboxylic amide or ester bond; and (b) to a ligand structurally analogous to the preselected amide or ester; the analog-ligand having a tetrahedrally bonded phosphorous atom located at the position occupied by the above-mentioned carbonyl carbon atom of the preselected carboxylic amide or ester bond of the before-mentioned ligand. The tetrahedrally bonded phosphorous atom is itself directly bonded to: (i) the alpha-carbon atom of the acid portion of the ligand by a single bond; (ii) a first oxygen atom that is doubly bonded to the phosphorous atom; (iii) a second oxygen atom that is bonded to the phosphorous atom by a single bond, and is singly bonded to a radical selected from the group consisting of $C_1$–$C_6$ lower alkyl, benzyl and phenyl; and (iv) a third oxygen atom or a nitrogen atom singly bonded to the phosphorous atom, and is also singly bonded to the alpha-carbon atom of the amine or alcohol portion of the ligand.

In preferred practice, the molecule exhibits lactone synthase activity. Thus, the ligand containing the carbonyl carbon is capable of forming a lactone, and the analog ligand is a phosphonate lactone, as exemplified by 2-phenoxy-2-oxo-6-acetamidomethyl-1,2-oxaphosphorinane.

The phrase "structurally capable of forming a preselected carboxylic amide or ester bond" is utilized herein to indicate that the structure of the ligand is such that it will permit and not inhibit, as by steric hinderance, the bond to be formed.

In another embodiment, this invention relates to a method of forming a preselected carboxylic ester or amide bond in a ligand molecule. The method comprises the steps of: (a) admixing an effective amount of one of the foregoing amide or ester synthase molecules in an aqueous medium with ligand molecules to form a reaction mixture; and (b) maintaining the reaction mixture for a period of time sufficient for the ligand molecules to bind to the receptor (synthase) molecule and for the receptor molecules to form the preselected bond. The reaction product containing the preselected amide or ester bond is thereafter preferably recovered.

The ester or amide bond-forming reaction is carried out in an aqueous medium that preserves the biological activity of the synthase molecule. Typically, such media are buffered to maintain a pH value near that of neutrality, such as between about pH values of about 6 and 8. More preferably, the pH value is about 6.5 to about 7.5.

Thus, the pH value of the aqueous medium is such that the activity of the synthase molecule is not substantially impaired during the catalytic reaction. Additionally, the aqueous medium is substantially free from salts, proteins, generally, and enzymes, specifically, that inhibit the bond-forming reaction catalyzed by the synthase molecule.

As discussed herein, exemplary receptor, molecules are secreted by a hybridoma designated 24B11 having ATCC accession number HB9488.

III Coupling of Compounds to Protein Carriers

Conjugates of haptenic analog-ligand molecules with protein carriers such as keyhole limpet hemocyanin (KLH) can be prepared, for example, by activation of the carrier with a linking agent such as MBS (m-maleimidobenzoyl-N-hydroxy succinimide ester), and coupling to the thiol group of the analog-ligand. See, for example, Liu et al., *Biochem.*, 80, 690 (1979). As is also well known in the art, it is often beneficial to bind a hapten to its carrier by means of a linking group that is reacted first with the hapten ad then the resulting hapten/linker is reacted with the antigenic carrier. Thus, the hapten is activated rather than the carrier. The acyl chloride portion of these linkers typically reacts first.

In addition to MBS, glutaraldehyde and other well known linking groups, two other linking groups have been found useful. These linkers are N-hydroxysuccinimidyl glutaryl chloride and N-hydroxysuccinimidyl adipoyl chloride whose syntheses are described herein.

Useful antigenic carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

The choice of carrier is more dependent upon the ultimate intended use of the antigen than upon the determinant portion of the antigen, and is based upon criteria not particularly involved in the present invention. For example, a carrier that does not generate an untoward reaction in the particular laboratory utilized animal should be selected.

The exemplary immunogenic conjugate was prepared from the phosphonate lactone by adapting its synthesis to incorporate a straight chain of carbon atoms on the methylene amino group of the lactone as a spacing element. It was concluded that the flexible carbon chain of an glutarate appendage would reduce any bias to immunoreactivity due to the conformational constraint imposed by covalent attachment to the carrier protein. The bifunctional reagent prepared for this purpose also delivers the preactivated carboxyl group for linkage via amide bond formation with the lysine residues of the carrier. The particular coupling method used in this study is further described herein. The phosphonate lactone was coupled to keyhole limpet hemocyanin (KLH) through a methylene amino group of the lactone.

According to the present invention, the intermediate linking agent is preferably succinimidyl glutaryl chloride that was prepared as described below.

The present invention is further illustrated by the examples that follow, which are not intended to be limiting.

EXAMPLE 1:

Preparation of Succinimidyl

Adipoyl Chloride (Linking Agent)

A solution of adipic acid monomethyl ester (5.4 g, 33.3 mmol) in thionyl chloride (15 ml) was heated at 40 degrees C. for 2 hours. The mixture was then concentrated and distilled in vacuo (boiling point 119 degrees C. at 20 mm Hg) to provide 3.58 g (60 percent yield by weight) of the acid chloride methyl ester. This was dissolved in 20 ml of dichloromethane and N-hydroxysuccinimide (2.75 g, 24.0 mmol) was added, followed by triethylamine (4.2 ml, 30 mmol). The mixture stirred for 10 minutes then diluted with ethyl acetate and washed with 0.5 M HCL and brine. The solution was dried over anhydrous magnesium sulfate, filtered and concentrated to give 4.5 g (87.5 percent yield by weight) of methyl succinimidyl adipate) as a colorless oil.

Proton NMR (in CDCl$_3$): delta 3.73 (singlet, 3H; delta 2.90 (singlet 4H), delta 2.70 (multiplet, 2H), delta 2.37 (multiplet, 2H), and delta 1.79 (multiplet 4H).

A solution of methyl succinimidyl adipate (4.5 g, 17.5 mmol), chlorotrimethylsilane (11.1 ml, 7.5 mmol) and sodium iodide (13.1 g, 87.5 mmol) in 10 ml of acetonitrile was heated at reflux for 12 hours. The mixture was then cooled to room temperature and diluted with ethyl acetate. The reaction mixture was washed repeatedly with 5 percent aqueous sodium bisulfite until the organic solution was colorless. Then it was washed with brine, dried over anhydrous magnesium sulfate, filtered and concentrated to provide 3.2 pg (71 percent yield by weight) of adipic acid monosuccinimidyl ester as a white solid.

Proton NMR (in CDCl$_3$) delta 3.90 (singlet, 4H), delta 2.70 (multiplet, 2H), delta 2.4 (multiplet, 2H), delta 1.80 (multiplet, 4H).

A mixture of adipic acid succinimidyl ester (1.00 g, 3.80 mmol) and thionyl chloride (5 ml) was heated at 40 degrees C. for 3 hours, then cooled to room temperature and concentrated in vacuo. The residue was stirred several times with dry hexane, the oil was separated and dried in vacuo to provide 0.97 g (90 percent yield by weight) of succinimidyl adipoyl chloride. This was dissolved in dry tetrahydrofuran to make a 5 Molar solution, which was used as such in the preparation of compounds suitable for coupling to protein carriers.

Proton NMR (in CDCl$_3$) delta 3.00 (multiplet, 2H), delta 2.90 (singlet, 4H), delta 2.70 (multiplet, 2H), delta 1.80 (multiplet 4H).

EXAMPLE 2:

N-Hydroxysuccinimidyl glutaryl chloride (Linking Agent)

One mole of glutaric anhydride and one mole of N-hydroxysuccinimide were treated in dichloromethane with 1.2 equivalents of triethylamine. This reaction was stirred for 40 minutes, acidified by the addition of 0.5 N hydrochloric acid (HCl) (aqueous), and then extracted with ethyl acetate to form mono N-hydroxysuccinimide glutarate. This glutarate was then combined with 5 moles of thionyl chloride and stirred at room temperature for three hours. The resulting reaction mixture was dried to remove volatiles, and thereby form N-hydroxysuccinimidyl glutaryl chloride.

EXAMPLE 3: 2-Phenoxy-2-oxo-6-aminomethyl 1,2-oxaphosphorinane

One mole of phenylphosphorodichloridite was combined with two moles of isopropanol and 2 moles of triethylamine, and reacted in diethylether for one hour at room temperature as described by Tolkwith et al., *J. Org. Chem.*, 23, 1682 (1958), to produce diisopropylphenylphosphite.

Three moles of this phosphite were mixed with one mole of 5-bromo-1-pentene and a catalytic amount of about 0.1 mole of sodium iodide, and heated at 185 degrees C. for three hours to produce phenyl isopropyl 4-pentenylphosphonate.

One mole of this phosphonate and 2.2 moles of iodine were stirred in chloroform at 10 degrees C. for four days as described by Zhao et al., *J. Org. Chem.*, 50, 2136 (1985) to produce 2-phenoxy-2-oxo-6-iodomethyl-1,2-oxaphosphorinane.

A suspension containing two moles of sodium axide, one mole of the above-prepared iodonated oxaphosphorinane and a catalytic amount of about 0.1 mole of tetrabutylammonium bromide in benzene/DMF (1:1) was heated to 60 degrees C. for 16 hours to produce 2-phenoxy-2-oxo-6-azidomethyl-1,2-oxaphosphorinane.

A solution of the above azide was prepared in ethanol containing 40 percent by weight of 10 percent palladium on carbon and shaken under 40 pounds per square inch (psi) of hydrogen gas for 20 hours at room temperature to produce the corresponding amine. A solution of the amine was then treated in ether with an excess of pyridinium bisulfate to precipitate the amine derivative by forming a bisulfate salt (2-phenoxy-2-oxo-6- aminomethyl-1,2-oxaphosphorinane bisulfate; Compound A bisulfate).

The salt so obtained was neutralized with 5 percent aqueous sodium bicarbonate, extracted into ethyl acetate, and recovered by evaporation of the solvent. The resulting dried amine (Compound A) was dissolved in dichloromethane and treated first with one mole of the N-hydroxysuccinimide (NHS) ester of glutaryl chloride and then with 1.2 moles of triethylamine to form the NHS-activated glutaramide.

Protein conjugates with phosphonate lactone of formula II wherein R was the described succinimidyl glutaryl chloride were prepared by the addition of 0.250 ml of a solution of the phosphonate in DMF [5 milligrams (mg)/ml]to 0.75 ml of a solution of protein (KLH or BSA, 3.33 mg/ml) in sodium phosphate buffer (pH 7.2, 0.2 M) and stirring gently for one hour at 22 degrees C.

The amine described above (Compound A) was also dissolved in dichloromethane and treated with acetic anhydride and triethylamine to form an acetamide derivative (formula II, where R is methyl). This derivative is utilized as an inhibitor.

EXAMPLE 4:

Phenyl-6-acetamido-5 trimethylsilyloxyhexanoate

One mole of mono methyl glutarate (Aldrich Chemical Corp., Milwaukee, Wisc.) was combined with 1.5 moles of thionyl chloride and stirred at room temperature for one hour to form methyl glutarylchloride. Volatile products were removed in vacuo from the resulting compound that was then treated with $Cu^ICN$ in acetonitrile at 80 degrees C. for 15 hours as described by Hunig et a., *Angew Chem. Int. Ed.* (Eng), 21, 36–49 (1982) (ref. 5), to form an acyl cyanide.

4.7 Grams of the acyl cyanide were shaken in 45 mililiters (ml) of acetic acid and 4.5 ml of acetic anhydride containing 5 percent palladium on carbon (1.12 gm) while under 40 psi of hydrogen gas to form methyl 6-acetamido-5-oxohexanoate. The resulting hexanoate was stirred in 95 percent ethanol containing 1.5 moles of potassium hydroxide for 5 minutes to form 6-acetamido-5-oxohexanoic acid. The resulting hexanoic acid was combined with, 1.5 moles of phenol and stirred with DCC and triethylamine in dichloromethane as described by Hassner et al, *Tet. Lett.*, 1978, 4475–4478 (1978) to form phenyl 6-acetamido-5-oxohexanoate. The resulting hexanoate was then combined with three moles of sodium cyanoborohydride, and while stirring, the pH value was maintained by the addition of a solution of methanolic HCl to form the corresponding alcohol. The alcohol (phenyl 6-acetamido-5-hydroxyhexanoate, formula I where R is methyl) was also converted to the corresponding phenyl 6-acetamido-5 trimethysilyloxyhexanoate as described by Sweely et al., *J. Am. Chem. Soc.*, 85, 2497 (1963) for storage, and was reconverted to the alcohol for use as a substrate ligand by reaction in 0.1 molar citric acid in methanol for 30 seconds at room temperature immediately prior to use.

EXAMPLE 5:

Preparation of Monoclonal Receptors

The foregoing KLH conjugates were used to immunize mice (129GlX+strain), and monoclonal antibodies were obtained as described by Niman et al., *Proc. Natl. Acad. Sci. USA*, 77, 4524 (1980) and Niman et al., in *Monoclonal Antibodies and T-Cell Products*, ed., Katz, D. H., 23–51 (CRC Press, Boca Raton, Fla. 1982).

The lymphocytes employed to form the hybridomas of the present invention, can be derived from any mammal, such as a primate, rodent (e.g., mouse or rat), rabbit, guinea pig, cow, dog, sheep, pig or the like. As appropriate, the host can be sensitized by injection of the immunogen, in this instance a haptenic analog-ligand, followed by a booster injection, and then isolation of the spleen.

It is preferred that the myeloma, cell line be from the same species as the lymphocytes. Therefore, fused hybrids such as mouse-mouse hybrids [Shulman et al., *Nature*, 276, 269 (1978)]or rat-rat hybrids [Galfre et al., *Nature*, 277, 131 (1979)]are typically utilized. However, some rat-mouse hybrids have also been successfully used in forming hybridomas [Goding, "Production of Monoclonal Antibodies by Cell Fusion," in *Antibody as a Tool*, Marchalonis et al. eds., John Wiley & Sons Ltd., p. 273 (1982)]. Suitable myeloma lines for use in the present invention include MPC-11 (ATCC CR1 167), P3X63-Ag8.653 (ATCC CR1 1580), Sp2/0-Ag14 (ATCC CRL 1581), P3 X 63 Ag8U.1 (ATCC CRL 1597), Y3-Ag1.2.3. (deposited at Collection Nationale de Cultures -de Microorganisms, Paris, France, number I-078) and P3X63Ag8 (ATCC TIB 9). The non-secreting murine myeloma line Sp2/0 or Sp2/0-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid were female 129GlX+mice bred in the mouse colony of the Scripps Clinic and Research Foundation, La Jolla, California, however, when animals other than mice are used for preparation of the hybridomas, mice or that animal type can be used for the production of ascites fluid.

In particular, exemplary monoclonal receptors were produced by the standard hybridoma technology of Kohler et al., *Nature*, 256, 495 (1975). For the preparation of the exemplary monoclonal receptor designated 24B11, the foregoing immunization protocol was modified as follows. Female 129GlX+mice were immunized by intraperitoneal injection with an inoculum of conjugate containing 60 micrograms (ug) of Compound X bound to 125 micrograms of KLH in 500 microliters (ul) of imulsion comprised of a 1:1 mixture of phosphate buffered saline (PBS) pH 7.4 and complete Freund's adjuvant. Two weeks later, the mice were again injected in a like manner with an innoculum containing one half the amount of original conjugate in 500 microliters of a solution of a 1:1 mixture of PBS (pH 7.4) and 10 mg/ml alum. After an additional four weeks, the mice were immunized intravenously with one and one-half times the amount of original conjugate in 500 microliters of PBS (pH 7.4). The spleens were removed from the mice 5 days later, and the spleens were fused to myeloma cells.

The spleens cells were pooled and a single cell suspension was made. Nucleated spleen cells ($1.4 \times 10^8$) were then fused with $3 \times 10^7$ Sp2/0 non-secreting myeloma cells in the presence of a cell fusion promoter (polyethylene glycol 2000.) The hybridoma that produces a particular monoclonal antibody was selected by seeding the spleen cells in 96-well plates and by growth in Dulbecco's modified Eagle medium (DMEM) containing 4500 mg/liter glucose (10 percent), 10 percent fetal calf serum (FCS), hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies against the immunizing analog-ligand. Positive wells were cloned twice by limiting dilution. Those clones that continued to produce analog-ligand-specific antibody after two clonings were expanded to produce larger volumes of supernatant fluid.

The hybridoma and the monoclonal receptors produced therefrom and described herein are identified by the designation 24B11, the particular material referred to being apparent from the context. Hybridoma 24B11 was deposited on Aug. 4, 1987 at the American Type Culture Collection, Rockville, Maryland and were given the ATCC accession number HB 9488.

The present deposits were made in compliance with the Budapest Treaty requirements that the duration of the deposits should be for 30 years from the date of deposit or for 5 years after the last request for the deposit at the depository or for the enforceable life of a U.S. Patent that matures from this application, whichever is longer. The hybridomas will be replenished should they become non-viable at the depository.

A monoclonal receptor of the present invention can be produced by introducing, as by injection, the hybridoma into the peritoneal cavity of a mammal such as a mouse. Preferably, as already noted, syngenic or semi-syngenic mammals are used, as in U.S. Pat. 4,361,549, the disclosure of which is incorporated herein by reference. The introduction of the hybridoma causes formation of antibody-producing hybridomas after a suitable period of growth, e.g. 1-2 weeks, and results in a high concentration of the receptor being produced that can be recovered from the bloodstream and peritoneal exudate (ascites) of the host mouse. Although the host mice also have normal antibodies in their blood and ascites, the concentration of normal antibodies is typically only about five percent that of the monoclonal receptor concentration.

The monoclonal receptor present in the hybridoma supernatant can be used without purification or the receptor can be recovered from the ascites or serum of the mouse using standard techniques such as affinity chromatography using AD 169-infected cells bound to an immunosorbant such Sepharose 6B or 4B (Pharmacia Fine Chemicals, Piscataway, NJ), followed by elution from the immunosorbant using an acidic buffer such as glycine hydrochloride at a pH value of about 2.5.

In the present studies, IgG fractions were obtained from mouse ascites by precipitation with 45 percent saturated ammonium sulfate followed by chromatography on DEAE-Sephacel with sodium chloride elution. The fraction that was eluted with 100 mM salt was dialyzed and concentrated. Stock solutions of antibody at 20 mg/ml were prepared in Tris-HCl (50 mM, pH 6.5). Protein concentrations were determined by the Lowry method. [*J. Biol. Chem.*, 193, 265 (1951)].

EXAMPLE 6:

Enzyme-linked Immunosorbent Assay (ELISA)

The binding of ligands and the effect of chemical modification were assayed by ELISA with antibody at fixed concentration in the range of its titer and varying reagent or ligand concentration. Inhibition is reported if the titer is reduced 50 percent at less than a 1000:1 ratio of reagent to hapten.

Assays were performed in flat-bottom polyvinyl microtiter plates (Dynatech, Alexandria, VA). The wells were coated with a solution comprising analog-ligand bound to BSA as the antigen ligand in phosphate buffered saline (PBS) using 50 microliters of solution per well. The ligand was coated at 1 microgram per milliliter. The plates were then incubated overnight at 37° C. in a dry oven. The dried plates were stored at 4° C. until use. Prior to the ELISA assay, dried plates were rehydrated by two washes of 2 minutes each with 10 millimola (mM) PBS, pH 7.4, containing 0.1 percent polyoxalkylene (20) sorbitan monolaurate (Tween 20) and 0.02 percent Thimerosal (sodium ethylmercurithiosalicylate), (Sigma, St. Louis, MO).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for 1 hour at 4° C. on a gyroshaker to contact the monoclonal antibody-containing supernatant with the bound analog-ligand. Following two washes of 2 minutes each, 50 microliters of peroxidase-labeled goat anti-mouse IgG +IgM (Tago, Burlingame, CA), diluted 1:1000, were added to each well, and the reaction mixture was incubated at 4° C. for 1 hour to bind the labeled antibody to bound monoclonal antibody.

The substrate used to assay bound peroxidase activity was prepared just prior to use and consisted of 400 microgram/ml o-phenylenediamine (Sigma, St. Louis, MO) in 80 mM citrate-phosphate buffer, pH 6.0,containing 0.12 percent $H_2O_2$. After two final washes, 50 microliters of substrate solution was added to each well and color was allowed to develop for 15 minutes in the dark. Color development was stopped by adding 25 microliters of 4 molar (M) $H_2SO_4$ to each well and the optical density at 492 nanometers (nm) was measured with a Multiskan ELISA plate reader. Polyclonal antibodies raised to the above analog-ligand were observed to immunoreact (bind) to the analog-ligand.

EXAMPLE 7:

Comparative Kinetic Studies

A first composition was prepared that contained about 0.5 mM of a ligand of formula I where R is methyl (phenyl 6-acetamido-5-hydroxyhexanoate) as substrate and 5 uM of a non-specific monoclonal antibody designated 24E12 in aqueous 50 mM phosphate as aqueous medium. This first composition was utilized as a control. A second composition was prepared that contained the same amount of substrate and 5 uM receptor 24B11 as a lactone synthase. A third composition was prepared identical to the second composition but further containing 20 uM of 2-phenoxy-2-oxo-6-acetamidomethyl-1,2-oxaphosphorinane (analog-ligand of formula II where R is methyl) as inhibitor.

The three compositions were maintained at room temperature and aliquots from each were taken at intervals to ascertain the concentration of substrate ligand remaining in each composition. Assays were carried out using HPLC (Hitachi) with a solvent containing 20 percent acetonitrile, 79.9 percent water and 0.1 percent trifluoroacetic acid, using a flow rate of 1.5 ml per minute. The detector was set at 225 nm. A C18 reverse phase column using Vidac 218TP54 as the solid phase was used.

Figure 2:
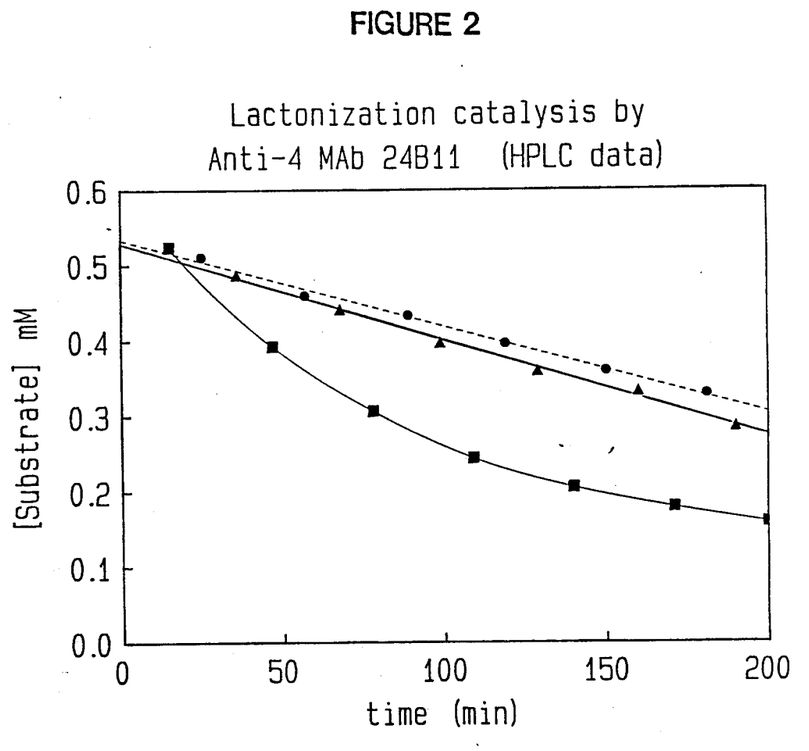
FIG. 2 is graph showing the decrease of ligand capable of forming a lactone shown in FIG. 1 (substrate) in reaction media over time in minutes (min.) in the presence of monoclonal antibody (Mab) 24B11 (closed squares), a control, non-specific monoclonal antibody (closed circles), and Mab 24B11 plus the immunizing ligand-analog as a competitive inhibitor (closed triangles). The substrate was initially present at about 0.5 millimolar (mM) in a 50 mM phosphate buffer (pH 7.0). The Mab 2411 or control monoclonal were present at 5 micromolar (uM), and the immunizing ligand-analog was present at 20 uM. The decrease in substrate concentration was determined by high pressure liquid chromatography (HPLC).

As can be seen from examination of the data of FIG. 2, the concentration of substrate ligand in above Compositions 1 (control) and 3 (substrate plus inhibitor) decreased at substantially identical rates. The decrease in substrate ligand in Composition 2 that contained the lactone synthase and no inhibitor decreased much more rapidly until about one-half of the substrate was consumed, and thereafter decreased at a rate similar to that of Compositions 1 and 3. (The background decreases in substrate in Compositions 1, 2 and 3 are thought to be due to non-specific hydrolysis of the phenyl ester.)

Since the substrate was present at a one hundred-fold excess over the receptor, and since at least one-half of the substrate was consumed relatively rapidly, the results shown in FIG. 2 indicate that the reaction involving the receptor was greater than stoichiometric and that true catalysis with turn over of the receptor catalyst with synthase activity was observed.

A likely explanation for the relatively rapid decrease to about one-half the initial concentration of substrate followed by the background substrate decrease is that the receptor synthase binds to the ligand substrate and catalyzes the lactone-forming reaction stereospecifically. Thus, the ligand has an asymmetric carbon atom at the 5-position where the hydroxyl, hydrogen and methylene acetamido groups are bonded to the chain. As a consequence, the ligand substrate exists as an enantiomeric pair. A similar enantiomeric pair exists for the analog-ligand utilized to induce production of the receptor lactone synthase.

If the receptor lactone synthase 24B11 secreted by hybribridoma 24B11 binds only one of the enantiomers of both the immunizing analog-ligand and substrate ligand, but not to the other enantiomer of either, it would be expected to catalyze lactone formation only by the substrate ligand to which it binds. Since each enantiomer constitutes one-half of the concentration of the enantiomeric pair, lactone formation of the bound enantiomer would be expected to be stereospecific and utilize only one-half of the admixed substrate ligand as is observed.

Figure 1:
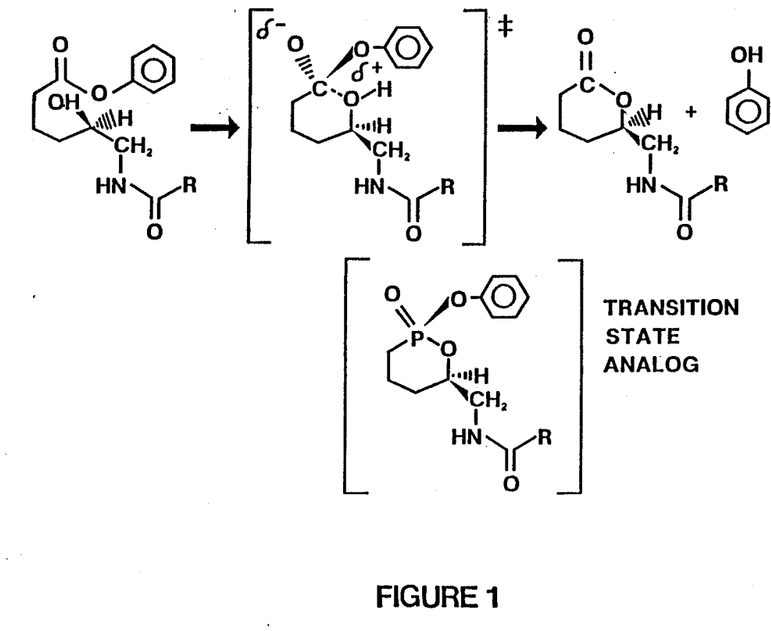

A schematic representation of the lactone synthase-catalyzed reaction illustrated for one enantiomer of the substrate ligand and one immunizing analog-ligand that is an analog to the lactone-foming transition state is shown in FIG. 1, using usual stereochemical depictions for chemical bonds. As is seen from that Figure, one enantiomer of the substate ligand (shown on the left) can form a transition state (shown in the brackets in the upper center of the Figure) that has a stereochemistry substantially identical to that of the analog-ligand (shown in brackets in the lower center). The lactone product (shown on the right of the Figure) is a single stereoisomer that retains the configuration of the ligand enantiomer that was bound and is shown on the left.

The foregoing is intended as illustrative of the present invention but not limiting. Numerous variations and modifications may be effected without departing from true spirit and scope of the invention.

What is claimed is:

1. An amide or ester synthase comprising a monoclonal receptor molecule containing an antibody combining site capable of catalyzing the formation of a preselected carboxylic amide or ester bond, said combining site binding:
   (a) to a ligand containing (i) a carbonyl carbon atom and (ii) an amine or alcohol group that are structurally capable of forming said preselected carboxylic amide or ester bond; and
   (b) to an analog-ligand wherein the analog-ligand is structurally analogous to said preselected amide or ester, said analog-ligand having a tetrahedrally bonded phosphorus atom located at the position occupied by said carbonyl carbon atom of said preselected carboxylic amide or ester bond of said ligand, said tetrahedrally bonded phosphorus atom being bonded directly to:
     (i) the alpha-carbon atom of the acid portion of said ligand by a single bond;
     (ii) a first oxygen atom that is doubly bonded to said phosphorous;
     (iii) a second oxygen atom that is bonded to said phosphorous atom by a single bond, and is singly bonded to a radical selected from the group consisting of $C_1$-$C_6$ lower alkyl, benzyl and phenyl; and
     (iv) a third oxygen atom or a nitrogen atom singly bonded to said phosphorous atom, and is also singly bonded to the alpha-carbon atom of the amine or alcohol portion of said ligand.

2. The synthase according to claim 1 that exhibits lactone synthase activity and wherein said ligand containing a carbonyl carbon is capable of forming a lactone and said analog-ligand is a phosphonate lactone.

3. The synthase according to claim 2 wherein said ligand has a structure of the formula and said analog-ligand has a structure of the formula wherein R is $C_1$-$C_6$ lower alkyl, or linking group bonded to an antigenic carrier protein; and $R^2$ is $C_1$-$C_6$ lower alkyl.

4. The synthase according to claim 3 wherein R and $R^2$ are methyl.

5. The synthase according to claim 1 wherein said monoclonal receptor molecule is an intact antibody.

6. A monoclonal receptor molecule secreted by a hybridoma designated 24B11 and HB9488, whose antibody combining site immunoreacts with a ligand having a structure of the formula

* * * * *

UNITED STATES PATENT AND TRADEMARK OFFICE
CERTIFICATE OF CORRECTION

PATENT NO. : 4,900,674
DATED : February 13, 1990
INVENTOR(S) : Stephen Benkovic et al.

It is certified that error appears in the above-identified patent and that said Letters Patent is hereby corrected as shown below:

Column 1, after the title and before the heading "TECHNICAL FIELD", insert the following paragraph:

--This invention was made with government support under Contract No. GM 35318 awarded by the National Institutes of Health and Contract No. DCB 8607352 awarded by the National Science Foundation. The government has certain rights in the invention.--

Signed and Sealed this

Twelfth Day of July, 1994

Attest:

BRUCE LEHMAN

*Attesting Officer*    *Commissioner of Patents and Trademarks*